United States Patent
Glatz et al.

(10) Patent No.: US 9,435,773 B2
(45) Date of Patent: Sep. 6, 2016

(54) SAMPLE INJECTOR WITH METERING DEVICE BALANCING PRESSURE DIFFERENCES IN AN INTERMEDIATE VALVE STATE

(75) Inventors: Bernd Glatz, Friolzheim (DE); Wolfgang Kretz, Waldbronn (DE)

(73) Assignee: Agilent Technologies, Inc., Santa Clara, CA (US)

( * ) Notice: Subject to any disclaimer, the term of this patent is extended or adjusted under 35 U.S.C. 154(b) by 673 days.

(21) Appl. No.: 13/375,884

(22) PCT Filed: Jun. 3, 2009

(86) PCT No.: PCT/EP2009/056795
§ 371 (c)(1),
(2), (4) Date: Feb. 15, 2012

(87) PCT Pub. No.: WO2010/139359
PCT Pub. Date: Dec. 9, 2010

(65) Prior Publication Data
US 2012/0132013 A1    May 31, 2012

(51) Int. Cl.
*G01N 30/20* (2006.01)
*G01N 30/32* (2006.01)
*G01N 30/36* (2006.01)
*G01N 30/02* (2006.01)

(52) U.S. Cl.
CPC .............. *G01N 30/20* (2013.01); *G01N 30/32* (2013.01); *G01N 30/36* (2013.01); *G01N 2030/027* (2013.01); *G01N 2030/207* (2013.01)

(58) Field of Classification Search
None
See application file for complete search history.

(56) References Cited

U.S. PATENT DOCUMENTS

| 4,068,528 A | 1/1978 | Gundelfinger |
| 4,182,184 A | 1/1980 | Bakalyar et al. |
| 4,939,943 A | 7/1990 | Strohmeier |
| 5,637,208 A | 6/1997 | Dourdeville |
| 6,012,487 A * | 1/2000 | Hauck ..................... 137/625.11 |
| 6,428,702 B1 * | 8/2002 | Berger et al. ................. 210/634 |
| 6,485,642 B2 | 11/2002 | Kaito et al. |

(Continued)

FOREIGN PATENT DOCUMENTS

| CN | 1327157 A | 12/2001 |
| DE | 102 22 334 A1 | 12/2003 |

(Continued)

OTHER PUBLICATIONS

European Office Action dated Oct. 18, 2012.

(Continued)

*Primary Examiner* — Robert R Raevis

(57) ABSTRACT

A sample injector (200) for use in a fluid separation system (10) for separating compounds of a fluidic sample in a mobile phase, the sample injector (200) comprising a switchable valve (202), a sample loop (204) in fluid communication with the valve (202) and configured for receiving the fluidic sample, a metering device (206) in fluid communication with the sample loop (204) and configured for introducing a metered amount of the fluidic sample on the sample loop (204), and a control unit (208) configured for controlling switching of the valve (202) to transfer the sample loop (204) between a low pressure state and a high pressure state via an intermediate state and for controlling the metering device (206) during the intermediate state to at least partially equilibrate a pressure difference in the sample loop (204) between the low pressure state and the high pressure state.

19 Claims, 9 Drawing Sheets

(56) References Cited

U.S. PATENT DOCUMENTS

| | | | |
|---|---|---|---|
| 7,588,725 | B2 | 9/2009 | Ozbal et al. |
| 8,806,922 | B2 * | 8/2014 | Hochgraeber ......... G01N 30/20 73/61.55 |
| 2003/0098076 | A1 | 5/2003 | Nichols |
| 2005/0194318 | A1 | 9/2005 | Ozbal et al. |
| 2007/0251302 | A1 | 11/2007 | Iwata |
| 2010/0288025 | A1 | 11/2010 | Hochgraeber |

FOREIGN PATENT DOCUMENTS

| | | |
|---|---|---|
| DE | 10 2004 052 584 A1 | 1/2006 |
| DE | 11 2005 000 128 T5 | 5/2007 |
| DE | 10 2007 059 651 A1 | 6/2009 |
| EP | 0244751 A2 | 4/1987 |
| EP | 0 244 751 A2 | 11/1987 |
| EP | 0321774 A2 | 6/1989 |
| EP | 0 327 658 A1 | 8/1989 |
| EP | 1 536 228 A1 | 6/2005 |
| EP | 1536228 A1 | 6/2005 |
| EP | 1577012 A1 | 9/2005 |
| EP | 2 051 071 A1 | 4/2009 |
| EP | 2051071 A1 | 4/2009 |
| EP | 2196801 A1 | 6/2010 |
| JP | 54-89692 A | 7/1979 |
| JP | 62-272155 A | 11/1987 |
| JP | 5-307026 A | 11/1993 |
| JP | 07072130 A | 3/1995 |
| JP | 2006-058146 A | 3/2006 |
| JP | 2008051746 A | 3/2008 |
| WO | 2004/025272 A1 | 3/2004 |
| WO | 2006/023828 A2 | 3/2006 |
| WO | 2006/083776 A2 | 8/2006 |
| WO | 2006083776 A2 | 8/2006 |
| WO | 2007/109529 A2 | 9/2007 |
| WO | 2007109529 A2 | 9/2007 |
| WO | 2008005845 A2 | 1/2008 |
| WO | 2008/103098 A1 | 8/2008 |
| WO | WO2009092345 A1 | 7/2009 |
| WO | 2009/108219 A2 | 9/2009 |

OTHER PUBLICATIONS

International Search Report from PCT/EP2009/056795 dated Jan. 13, 2010 (4 pages).
Japanese Office Action dated Oct. 11, 2013.
Chinese Office Action dated Oct. 15, 2013.
Espacenet Abstract Publication No. JP2006058146A dated Mar. 2, 2006 (1 page).
Espacenet Abstract Publication No. JP5307026A dated Nov. 19, 1993 (1 page).
Espacenet Abstract Publication No. JP54089692A dated Jul. 16, 1979 (1 page).
Espacenet Abstract Publication No. JP62272155A dated Nov. 26, 1987 (1 page).
Espacenet Abstract Publication No. DE10222334A1 dated Dec. 4, 2003 (2 pages).
Espacenet Abstract Publication No. 112005000128T5 dated May 3, 2007 (1 page).
Espacenet Abstract Publication No. DE102007059651A1 dated Jun. 18, 2009 (1 page).
Espacenet Abstract Publication No. DE102004052584A1 dated Jan. 12, 2006 (1 page).
EP Communication dated Jun. 27, 2013.
Australian Examination dated Jun. 26, 2014.
Chinese Office Action with translation dated Jul. 10, 2014.
Canadian Office Action dated Jul. 10, 2015.
"Agilent 1100 Series HPLC Value System", Agilent Technologies, Inc., pp. 1-76.
Angelika Gratzfeld-Huesgen et al., "Agilent 1200 Series Rapid Resolution LC and Rapid Resolution LC/MS Optimization Guide", Agilent Technologies, www.agilent.com, pp. 1-133.
"Agilent 1200 Series HPLC-Chip/MS system", Agilent Technologies, Aug. 1, 2008, http://www.chem.agilent.com/Scripts/PDS.asp-?lPage=38308, pp. 1-8.
Final Office action dated Mar. 2, 2016 from related U.S. Appl. No. 14/877,758, filed Oct. 7, 2015.
Final Office action dated Jun. 14, 2016 from related U.S. Appl. No. 14/877,758, filed Oct. 7, 2015.

* cited by examiner

SAMPLE INJECTOR WITH METERING DEVICE BALANCING PRESSURE DIFFERENCES IN AN INTERMEDIATE VALVE STATE

CROSS REFERENCE TO RELATED APPLICATIONS

This is a national stage application of PCT/EP2009/056795, filed on Jun. 3, 2009, the disclosure of which is incorporated by reference in its entirety.

BACKGROUND ART

The present invention relates to sample injectors, in particular in a high performance liquid chromatography application.

In high performance liquid chromatography (HPLC, see for instance http://en.wikipedia.org/wiki/HPLC), a liquid has to be provided usually at a very controlled flow rate (e.g. in the range of microliters to milliliters per minute) and at high pressure (typically 20-100 MPa, 200-1000 bar, and beyond up to currently 200 MPa, 2000 bar) at which compressibility of the liquid becomes noticeable. For liquid separation in an HPLC system, a mobile phase comprising a sample fluid with compounds to be separated is driven through a stationary phase (such as a chromatographic column), thus separating different compounds of the sample fluid.

Valves are commonly used in HPLC applications, for instance injection valves for introducing a liquid sample into a high pressure flowing stream of liquid, a purge valves for positive displacement pumps, flow path switching valves, etc. Such valves used in HPLC applications are often multi-position rotary valves. Examples of multi-position rotary valves are disclosed in U.S. Pat. No. 4,068,528 A (two-position valves) or US 2003/0098076 A1 (multi-function rotary valves or random-access, dual, three-way, rotary switching valves).

Shear valves, which can be used in multi-way embodiments, are usually formed by a housing and a body defining a stepped cavity in which the rotor or seal is positioned. The housing contains at least two shear seal valve members positioned to be aligned with ports in the rotor (body) to establish communication between the shear seal means. Shear valves are usually provided as rotary valves (such as the aforementioned rotary valves) or translational valves (often also called sliding valves), such as disclosed in EP 0321774 A2.

A multi-way switching valve provides a means for selectively routing a fluid input flow to the valve to one of more alternate output flows from the valve. A rotary valve is of the type wherein fluid flow is directed by rotating a valve rotor element to discrete angular positions relative to a stationary valve stator element. A dual rotary valve provides two valves in one valve body, both simultaneously operated by the positioning of the valve rotor. Rotary switching valves are commonly used, for example, in HPLC and other analytical methods to selectively direct a flow stream of one or more fluids along alternate paths to an analytical device or containment vessel.

The aforementioned US 2003/0098076 A1 shows in its FIG. 1 a conventional type of dual, three-way, switching valve 220, which includes a disc-shaped rotor with a set of rotor grooves in the front face of the rotor that contacts, in a fluid-tight manner, the face of a cylindrically shaped stator body at a rotor-stator interface. Inlet passages and outlet passages, longitudinally bored through the stator body to the rotor-stator interface, are selectively fluidly coupled through the rotor grooves corresponding to the rotation of the rotor relative to the stator. Pivoting of the rotor enables the rotor grooves to fluidly couple selected passages of the stator, depending on their placement on the rotor and the angular position of the valve rotor. Model 7030 of Rheodyne, L. P. is an example of this type of switching valve.

WO 2007/109529 discloses methods and apparatus for placing a sample in a chromatographic system. The device and method feature placing samples held in a sample loop to pressurization prior to placing such sample loop in communication with high pressure conduits.

WO 2008/005845 discloses a method for processing a fluid applied to systems that include a valve unit that has a sample-loading state and a sample-introducing state. The sample-loading state disposes a sample loop in fluidic communication with a sample conduit. The sample-introducing state disposes the sample loop in fluidic communication with a process conduit. The method involves transferring a sample through both the sample conduit and the valve unit so that a leading end of the sample exits the valve unit. After transitioning the valve unit to the sample-loading state and allowing the sample loop to decompress, at least some of the transferred sample is loaded into the sample loop. A fluid-processing instrument includes a value unit and a control unit that manages operation of the instrument. The control unit is configured, for example, to implement the above-described method.

WO 2006/083776 discloses a method and apparatus for substantially eliminating destructive transients of pressure or flow rate which can degrade the efficiency and useful lifetime of chromatography columns. The system enables a substantially constant flow of mobile phase liquid to be maintained through the chromatography system by eliminating the flow blockage interval associated with the actuation of sample injection valves. The system further provides a method to reduce the pressure and flow rate transients associated with pressurization of the sample loop contents when the sample loop is introduced to chromatography system delivery pressure.

WO 2006/023828 discloses systems, devices, and methods to mitigate the pressure disturbance associated with the injection of low-pressure analyte samples into a high-pressure HPLC fluid stream, to enhance chromatographic performance related to retention time and reproducibility. An embodiment coordinates the injection run with active pressure control of a binary solvent delivery system to virtually eliminate the customary pressure drop when the low-pressure loop is brought on line. An additional feature is accomplished by forcing a consistent timing relationship between the injection run, the mechanical position of the delivery pump pistons, and the start and subsequent gradient delivery.

US 2007/0251302 discloses a flow path switching valve in which an impact due to the pressure change when a flow path is switched is prevented from being generated. A rotor slot allows an analysis infusion pump to be connected to an analytical column, so as to form a flow path (condensing procedure). The rotor of the flow path switching valve is rotated clockwise for 30 degrees, and the rotor slot allows the analysis infusion pump, the analytical column, and a trap column to be connected. After the pressure in the trap column is raised to the same pressure level as that of the analytical column, the pressure is stabilized, and the pressure difference between the two columns is counteracted (high-pressure procedure). After the pressure between the two columns has been stabilized sufficiently, the rotor is further rotated for 30 degrees, and the trap column and the analytical column are connected in series, so the sample analysis can be performed (dissolution procedure and detection procedure).

In modern HPLC with pressures rising up to 100 MPa and beyond, life time of sample injectors becomes critical, in particular for the injection valve, as a high pressure load acts on the components particularly when switching between a high pressure operation mode and a low pressure operation mode, which causes excessive wear.

DISCLOSURE

It is an object of the invention to provide an improved sample injector, in particular for high pressure HPLC applications.

According to an embodiment of the present invention, a sample injector for use in a fluid separation system for separating compounds of a fluidic sample in a mobile phase is provided, the sample injector comprising a switchable valve (i.e. a valve switchable between multiple positions, wherein each position corresponds to an assigned fluid coupling/decoupling characteristic of conduits connectable to the valve), a sample loop in fluid communication with the valve and configured for receiving the fluidic sample, a metering device in fluid communication with the sample loop and configured for introducing a metered amount (for instance a predefined volume or mass) of the fluidic sample on the sample loop, and a control unit configured for controlling switching of the valve to transfer the sample loop between a low pressure state (at which the sample loop may be at a first pressure value) and a high pressure state (at which the sample loop may be at a second pressure value larger than the first pressure value) via an intermediate state and for controlling the metering device during the intermediate state to at least partially (i.e. partially or entirely) equilibrate a pressure difference in the sample loop between the low pressure state and the high pressure state.

According to another embodiment of the present invention, a fluid separation system for separating compounds of a fluidic sample in a mobile phase is provided, the fluid separation system comprising a mobile phase drive (such as a pumping system) adapted to drive the mobile phase through the fluid separation system, a separation unit (such as a chromatographic column) adapted for separating compounds of the fluidic sample in the mobile phase, and a sample injector having the above mentioned features for introducing the fluidic sample into the mobile phase.

According to still another embodiment of the present invention, a method of operating a sample injector in a fluid separation system for separating compounds of a fluidic sample in a mobile phase is provided, wherein the method comprises introducing, by a metering device, a metered amount of the fluidic sample on a sample loop in fluid communication with a switchable valve and the metering device, controlling switching of the valve to transfer the sample loop between a low pressure state and a high pressure state via an intermediate state, and controlling the metering device during the intermediate state to at least partially equilibrate a pressure difference in the sample loop between the low pressure state and the high pressure state.

According to an exemplary embodiment, a switchable valve, a sample loop and a metering device may be arranged in a configuration in which they are always in fluid communication with one another regardless of a present switching state of the valve. The system may be switchable between two or more pressure modes, particularly between a high pressure mode and a low pressure mode. Exemplary embodiments may allow to suppress or even eliminate undesired pressure drops and consequently undesired cavitation effects (such as bubble implosions in the switchable valve or the sample loop in response to a sudden change of the pressure conditions) by softly equilibrating the pressure difference between the two pressure modes in a dedicated intermediate valve state so that a smooth balancing of pressure differences between the low pressure state and the high pressure state can be achieved. Cavitation effects may deteriorate or even delaminate a coating of the valve. By preventing cavitation effects, the lifetime of the sample injector and particularly of the switchable valve may be significantly increased. Furthermore, a sudden pressure increase or decrease may result in disturbances in a flow profile, and may interrupt a column flow during the switching procedure. Also such undesired effects may be efficiently suppressed by exemplary embodiments.

In the following, further exemplary embodiments of the sample injector will be explained. However, these embodiments also apply to the fluid separation system and to the method.

According to an exemplary embodiment, the control unit may be configured for controlling switching of the valve to transfer the sample loop from the high pressure state to the low pressure state via the intermediate state and for controlling the metering device during the intermediate state to perform a decompression (or pressure reduction) in the sample loop before transferring the sample loop to the low pressure state. In such an embodiment, the smooth equilibration starts in a high pressure state in which a high pressure of for instance 100 MPa is present at the sample loop and decompresses the sample loop for reducing the pressure towards or down to a low pressure (for instance an atmospheric pressure) before initiating the switching to the actual low pressure state. This may safely prevent sudden decompression of a fluid which may occur in the sample loop when switching from the high pressure to the low pressure.

Still referring to the previous embodiment, the control unit may be configured for controlling the metering device for performing the decompression by retracting a metering piston of the metering device. Hence, the metering device which is present in the sample injector predominantly for introducing a sample from a vial or the like into the sample loop by retracting and forwarding a metering piston, may be used as well for performing the decompression prior to the switching. Hence, the metering device can be synergistically used for both purposes of sample introduction and pressure equilibration.

Additionally or alternatively, the control unit may be configured for controlling switching of the valve to transfer the sample loop from the low pressure state to the high pressure state via the intermediate state and for controlling the metering device during the intermediate state to perform a precompression in the sample loop before transferring the sample loop to the high pressure state. Hence, the pressure equilibration feature can be applied also in a configuration in which a switch from the low pressure state to the high pressure state is initiated so that in the intermediate valve state the pressure may be slowly or continuously increased so that a subsequent switch from the intermediate state to the high pressure state of the valve does not generate an intense pressure pulse since the pressure difference has already been equilibrated smoothly beforehand.

Still referring to the previous embodiment, the control unit may be configured for controlling the metering device for performing the precompression by pushing forward the metering piston. As mentioned above, the metering device may predominantly act for introducing a sample from a vial into the sample loop but may be, according to the described exemplary embodiment, used as well for effecting a pressure increase in the sample loop during the intermediate state for reducing a mechanical load which conventionally acts on the components of the sample injector upon suddenly switching from the low pressure mode to the high pressure mode.

In an embodiment, the metering device may be configured as a high pressure metering device. In other words, the metering device may be configured for providing pressure values which are significantly higher than only several bars, thereby providing the structural and functional capability of equilibrating the pressure in the sample loop between high and low pressure modes with typical pressure values which can be present in the sample injector of a liquid chromatography device such as a HPLC. This may require to substitute conventional metering devices (like syringe pumps, capable of operating at a pressure value of several bars only) by a high pressure metering device which may be capable of providing significantly larger pressures such as about 10 MPa, particularly at least about 50 MPa, more particularly at least about 100 MPa or more.

The metering device may be configured for providing basically the same pressure as a mobile phase drive, particularly a pumping system, adapted to drive a mobile phase through a separation column of the fluid separation system. Such a mobile phase drive may be provided to drive a mobile phase such as a solvent composition comprising, for instance, a mixture of water and an organic solvent such as ACN, for conducting the same through a separation column of a liquid chromatography device. The mentioned metering device may provide a pressure of for instance 100 MPa, whereas sample introduction into the sample loop using a metering device is in many conventional cases performed not significantly above an atmospheric pressure or the like. Hence, the metering device may then be operated in different pressure modes, for instance a low pressure mode for introducing a sample from a vial or the like into the sample loop or in a high pressure state for bringing the sample loop smoothly to a high pressure value as provided by the mobile phase drive before switching a valve from an intermediate to a high pressure state.

The metering device may also be configured for increasing a pressure in the sample loop, before switching the sample loop from the low pressure state to the high pressure state, to or towards a system pressure of a mobile phase drive, particularly a pumping system, adapted to drive a mobile phase through a separation column of the fluid separation system. Hence, the metering device may dampen the pressure drop between a mode in which the sample loop is in fluid communication with the mobile phase drive and a mode in which the sample loop is out of fluid communication with the mobile phase drive.

According to an exemplary embodiment, the valve may comprise a first valve member and a second valve member, wherein at least one of the first and the second valve members is adapted to be moved with respect to the other, wherein one of the first and second valve members comprises a plurality of ports and the other comprises at least one groove for fluidly coupling respective ones of the ports in dependency on a relative movement position of the first and the second valve members with respect to each other. In other words, fluid paths may be formed by at least two of the ports and at least one of the grooves which can selectively be brought in or out of fluid communication with these ports.

In contrast to conventional approaches in which such a valve only has an initial state and a final state and a switching between the initial state and the final state suddenly increases or decreases a pressure, a valve according to an exemplary embodiment may have a stable intermediate state between the initial and the final state to which intermediate state the valve may be brought for performing equilibration between a high pressure and a low pressure using the metering device in the sample loop.

Still referring to the previous embodiment, the plurality of ports and the at least one groove may be designed so that in the intermediate state of the sample loop succeeding the low pressure state and preceding the high pressure state of the sample loop, a pumping system adapted to drive the mobile phase through a separation column is still in fluid communication with the separation column, and the sample loop is no longer at an atmospheric pressure and not yet in fluid communication with the separation column. Such an embodiment corresponds to a switch from a bypass mode to a main pass mode (for instance to a switch from FIG. 4 via FIG. 3 to FIG. 2). Therefore, in the intermediate state, the sample loop may still be fluidly decoupled from the pumping system but can be already brought to a higher pressure as compared to 1 bar before being switched to the start/inject state.

Additionally or alternatively, the plurality of ports and the at least one groove may further be designed so that in the intermediate state of the sample loop succeeding the high pressure state and preceding the low pressure state of the sample loop, a pumping system adapted to drive the mobile phase through a separation column is still in fluid communication with the separation column, and the sample loop is no longer at a pressure of the pumping system and not yet at an atmospheric pressure. Such an embodiment corresponds to a switch from a main pass mode to a bypass mode (for instance to a switch from FIG. 2 via FIG. 3 to FIG. 4). Therefore, in the intermediate state, the sample loop may be already fluidly decoupled from the pumping system and can be already brought to a lower pressure before being switched to the loading state.

The plurality of ports and the at least one groove may be designed so that in the high pressure state, the sample loop is in fluid communication with a pumping system adapted to drive a mobile phase drive through a separation column and is in fluid communication with the separation column. Thus, the high pressure state may be characterized by a fluid communication between the mobile phase drive and the sample loop.

The plurality of ports and the at least one groove may further be designed so that in the low pressure state, the sample loop is not in fluid communication with a pumping system adapted to drive a mobile phase through a separation column and is not in fluid communication with the separation unit. Thus, the low pressure state can be characterized by the absence of the high pressure of the mobile phase drive in the sample loop.

Moreover, the plurality of ports and the at least one groove may be designed so that a first position of one of the at least one groove is aligned with one of the plurality of ports in the low pressure state, a second position of the one of the at least one groove is aligned with the one of the plurality of ports in the high pressure state, and a third position (differing from the first and second positions) of the one of the at least one groove is aligned with the one of the plurality of ports in the intermediate state. In such an embodiment, a stop position of the one of the plurality of ports may be defined (particularly not only at the first and the second position but also) at a third position of the one of the at least one groove. Therefore, an intermediate valve state may be provided which represents a state selectable by the control unit during which an equilibration between a high pressure and a low pressure may be performed within the sample loop.

In an embodiment, different ones of the plurality of grooves may have different lengths. Therefore, by length selection and also geometry selection (the grooves may have an arcuate partial circle like appearance but can also have further geometrical features such as a hook or the like), additional design parameters for valve configuration are provided which allow to properly define intermediate state, initial state, end state and optionally further states of the valve.

Optionally, a pressure sensor may be arranged in the sample loop (particularly between the metering device and the switchable valve) for measuring a pressure in the sample loop. The pressure sensor may provide a measured pressure to the control unit as a feedback signal as a basis for the controlling of at least one of the metering device and the valve.

The low pressure may be smaller than the high pressure. For example, the low pressure may be an atmospheric pressure (of about 0.1 MPa), whereas the high pressure may be at least 50 MPa, more particularly at least about 100 MPa. With such pressure drops between atmospheric pressure and 50 MPa or even 100 MPa, strong and destructive cavitation effects may occur without the pressure equilibration according to an exemplary embodiment.

According to one embodiment, the valve may comprise six ports and two grooves. In such a configuration which is shown in the embodiment of FIG. 2 to FIG. 4 for example, the intermediate state may be arranged between two other valve states.

In an alternative embodiment, which is illustrated in FIG. 5 to FIG. 9, the valve may comprise seven ports, three grooves and may be switchable between six (or more) positions. With such a configuration, the pressure equilibration feature may be further refined.

The low pressure state of the sample loop may correspond to an operation mode in which the fluidic sample is loaded onto the sample loop and the mobile phase is driven by a mobile phase drive, particularly a pumping system, through a separation column of the fluid separation system. In such an operation mode, a needle can be lifted out of a seat in the sample loop and may be immersed into a vial or the like for loading the sample on the sample loop, which may occur at a relatively low pressure of for instance one atmosphere.

In contrast to this, the high pressure state of the sample loop may correspond to an operation mode in which the fluidic sample is injected from the sample loop to the separation column and is driven by a mobile phase drive, particularly a pumping system, to be loaded onto the separation column of the fluid separation system. In such an embodiment, the sample which has previously been loaded in the sample loop may then be pumped onto a separation column using the high pressure of the mobile phase drive. Subsequently, the different fractions of the sample which are then retained at fluid separation beads of the separation column may be individually and separately be released from the separation column by a gradient run, i.e. by a variation of a solvent which may be subsequently pumped through the separation column by the mobile phase drive.

Optionally, the sample injector may comprise a flush conduit configured for flushing at least a part of fluidic conduits of the sample injector. For example for cleaning or rinsing purposes, a flush loop may be provided which allows to clean such fluidic conduits to prevent carryover or the like. Such a flush loop may be properly implemented in the pressure equilibration system according to an exemplary embodiment.

In an embodiment, the metering device is arranged within the sample loop. In other words, in the described embodiment metering device and sample loop may be always in fluid communication with one another regardless of a switching state of the valve. This architecture may allow for a very simple equilibration of the pressure in the sample loop when transferring the sample loop between a high pressure mode and a low pressure mode.

According to an exemplary embodiment, an appropriate groove design in a valve may allow to provide an additional intermediate position at which the pump may still be connected with the column and the split loop may be not yet connected with the pump and may be no more connected with a waste (atmospheric pressure). When providing a high pressure capable metering device in the split loop, i.e. a high pressure metering device capable of providing the same pressures as a column pump, it is possible to balance out pressure differences before the switching. For instance, such a high pressure metering device may displace a volume of for example 2 µl to 10 µl with a pressure of about 100 MPa. To achieve such a performance, it is possible to position the high pressure metering device (particularly a piston position thereof) in such a manner that the compression of 2 µl to 10 µl is possible.

In one embodiment, the shear valve is embodied as a rotary valve, with the first and second shear valve members being rotably moveable with respect to each other. In another embodiment, the shear valve is embodied as a translational valve, such as a slide valve, with the first and second shear valve members being translationally moveable with respect to each other.

In one embodiment, the shear valve further comprises a housing for housing one of the first and second shear valve members, wherein the housing is pre-stressed (pre-loaded) against the housed shear valve member. This allows reducing breakage or fracture stress, which may occur in the housed shear valve member. The housing is preferably attached to the housed shear valve member by using a shrinking process as known in the art.

In one embodiment, the fluid path of this shear valve comprises a groove. In one embodiment, one or more of the ports of the shear valve comprise a through hole having an opening fluidly coupling with the fluid path dependent on the moving position. In one embodiment, wherein the first shear valve member comprises a plurality of ports, the second shear valve member comprises the at least one fluid path for fluidly coupling respective ones of the port in dependency on a relative movement position of the first and second shear valve member with respect to each other. In a further embodiment, the second shear valve member is adapted to be moved with respect to the first shear valve member. Preferably, the second shear valve member is provided as a rotor or slider moving on the first shear valve member, which is embodied as a static member and not moving. A drive might be provided for moving the shear valve member to be moved. Alternatively or in addition, the shear valve member to be moved might also be moved manually. A valve drive and control unit (e.g., gearbox+motor+encoder+central processing unit, CPU), might be provided for controlling movement of the shear valve member to be moved.

The shear valve is preferably adapted to conduct a liquid in the at least one fluid path at a high pressure at which compressibility of the liquid becomes noticeable, such as pressure in the range of 20-200 MPa, and particularly 50-120 MPa.

The shear valve can be a sample injection valve for introducing a liquid sample into a high pressure flowing stream of liquid, a high pressure purge valve for a positive displacement pump, or a flow path switching valve for switching from one flow path to another flow path.

The shear valve might be embodied in an HPLC sample injector adapted to introduce a sample fluid into a mobile phase. The mobile phase is to be driven by a mobile phase drive through a separation unit for separating compounds of the sample fluid in the mobile phase. A sample loop is provided for receiving the sample fluid. The shear valve is provided for switching the sample loop between the mobile phase drive and the separation unit for introducing the sample fluid into the mobile phase.

Embodiments of the present invention might be embodied based on most conventionally available HPLC systems, such as the Agilent 1200 Series Rapid Resolution LC system or the Agilent 1100 HPLC series (both provided by the applicant Agilent Technologies—see www.agilent.com—which shall be incorporated herein by reference).

One embodiment comprises a pumping apparatus having a piston for reciprocation in a pump working chamber to compress liquid in the pump working chamber to a high pressure at which compressibility of the liquid becomes noticeable.

One embodiment comprises two pumping apparatuses coupled either in a serial or parallel manner. In the serial manner, as disclosed in EP 309596 A1, an outlet of the first pumping apparatus is coupled to an inlet of the second pumping apparatus, and an outlet of the second pumping apparatus provides an outlet of the pump. In the parallel manner, an inlet of the first pumping apparatus is coupled to an inlet of the second pumping apparatus, and an outlet of the first pumping apparatus is coupled to an outlet of the second pumping apparatus, thus providing an outlet of the pump. In either case, a liquid outlet of the first pumping apparatus is phase shifted, preferably essentially 180 degrees, with respect to a liquid outlet of the second pumping apparatus, so that only one pumping apparatus is supplying into the system while the other is intaking liquid (for instance from the supply), thus allowing to provide a continuous flow at the output. However, it is clear that also both pumping apparatuses might be operated in parallel (i.e. concurrently), at least during certain transitional phases for instance to provide a smooth(er) transition of the pumping cycles between the pumping apparatuses. The phase shifting might be varied in order to compensate pulsation in the flow of liquid as resulting from the compressibility of the liquid. It is also known to use three piston pumps having about 120 degrees phase shift.

The separating device preferably comprises a chromatographic column (see for instance http://en.wikipedia.org/wiki/Column chromatography) providing the stationary phase. The column might be a glass or steel tube (for instance with a diameter from 50 μm to 5 mm and a length of 1 cm to 1 m) or a microfluidic column (as disclosed for instance in EP 1577012 or the Agilent 1200 Series HPLC-Chip/MS System provided by the applicant Agilent Technologies, see for instance http://www.chem.agilent.com/Scripts/PDS.asp?lPage=38308). For example, a slurry can be prepared with a powder of the stationary phase and then poured and pressed into the column. The individual components are retained by the stationary phase differently and separate from each other while they are propagating at different speeds through the column with the eluent. At the end of the column they elute one at a time. During the entire chromatography process the eluent might be also collected in a series of fractions. The stationary phase or adsorbent in column chromatography usually is a solid material. The most common stationary phase for column chromatography is silica gel, followed by alumina. Cellulose powder has often been used in the past. Also possible are ion exchange chromatography, reversed-phase chromatography (RP), affinity chromatography or expanded bed adsorption (EBA). The stationary phases are usually finely ground powders or gels and/or are microporous for an increased surface, though in EBA a fluidized bed is used.

The mobile phase (or eluent) can be either a pure solvent or a mixture of different solvents. It can be chosen for instance to minimize the retention of the compounds of interest and/or the amount of mobile phase to run the chromatography. The mobile phase can also been chosen so that the different compounds can be separated effectively. The mobile phase might comprise an organic solvent like for instance methanol or acetonitrile, often diluted with water. For gradient operation water and organic is delivered in separate bottles, from which the gradient pump delivers a programmed blend to the system. Other commonly used solvents may be isopropanol, THF, hexane, ethanol and/or any combination thereof or any combination of these with aforementioned solvents.

The sample fluid might comprise any type of process liquid, natural sample like juice, body fluids like plasma or it may be the result of a reaction like from a fermentation broth.

The pressure in the mobile phase might range from 2-200 MPa (20 to 2000 bar), in particular 10-150 MPa (100 to 1500 bar), and more particular 50-120 MPa (500 to 1200 bar).

The HPLC system might further comprise a sampling unit for introducing the sample fluid into the mobile phase stream, a detector for detecting separated compounds of the sample fluid, a fractionating unit for outputting separated compounds of the sample fluid, or any combination thereof. Further details of HPLC systems are disclosed with respect to the Agilent 1200 Series Rapid Resolution LC system or the Agilent 1100 HPLC series, both provided by the applicant Agilent Technologies, under www.agilent.com which shall be incorporated herein by reference.

Embodiments of the invention can be partly or entirely embodied or supported by one or more suitable software programs, which can be stored on or otherwise provided by any kind of data carrier, and which might be executed in or by any suitable data processing unit. Software programs or routines can be preferably applied in or by the control unit.

BRIEF DESCRIPTION OF DRAWINGS

Other objects and many of the attendant advantages of embodiments of the present invention will be readily appreciated and become better understood by reference to the following more detailed description of embodiments in connection with the accompanied drawing(s). Features that are substantially or functionally equal or similar will be referred to by the same reference sign(s).

Referring now in greater detail to the drawings, FIG. 1 depicts a general schematic of a liquid separation system 10. A pump 20 receives a mobile phase from a solvent supply 25, typically via a degasser 27, which degases and thus reduces the amount of dissolved gases in the mobile phase. The pump 20—as a mobile phase drive—drives the mobile phase through a separating device 30 (such as a chromatographic column) comprising a stationary phase. A sampling unit 40 (compare the detailed description of FIG. 2 to FIG. 9) can be provided between the pump 20 and the separating device 30 in order to subject or add (often referred to as sample introduction) a sample fluid into the mobile phase. The stationary phase of the separating device 30 is adapted for separating compounds of the sample liquid. A detector 50 is provided for detecting separated compounds of the sample fluid. A fractionating unit 60 can be provided for outputting separated compounds of sample fluid.

Figure 1:
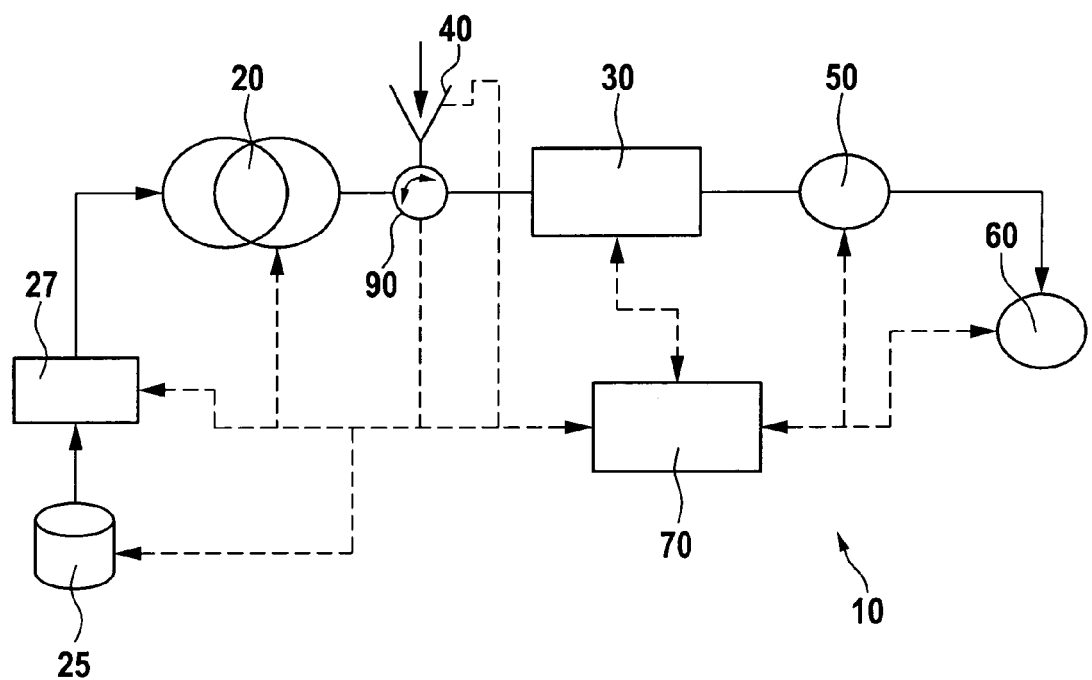
FIG. 1 shows a liquid separation system, in accordance with embodiments of the present invention, for instance used in high performance liquid chromatography (HPLC).

While the mobile phase can be comprised of one solvent only, it may also be mixed from plural solvents. Such mixing might be a low pressure mixing and provided upstream of the pump 20, so that the pump 20 already receives and pumps the mixed solvents as the mobile phase. Alternatively, the pump 20 might be comprised of plural individual pumping units, with plural of the pumping units each receiving and pumping a different solvent or mixture, so that the mixing of the mobile phase (as received by the separating device 30) occurs at high pressure and downstream of the pump 20 (or as part thereof). The composition (mixture) of the mobile phase may be kept constant over time, the so called isocratic mode, or varied over time, the so called gradient mode.

A data processing unit 70, which can be a conventional PC or workstation, might be coupled (as indicated by the dotted arrows) to one or more of the devices in the liquid separation system 10 in order to receive information and/or control operation. For example, the data processing unit 70 might control operation of the pump 20 (for instance setting control parameters) and receive therefrom information regarding the actual working conditions (such as output pressure, flow rate, etc. at an outlet of the pump). The data processing unit 70 might also control operation of the solvent supply 25 (for instance setting the solvent/s or solvent mixture to be supplied) and/or the degasser 27 (for instance setting control parameters such as vacuum level) and might receive therefrom information regarding the actual working conditions (such as solvent composition supplied over time, flow rate, vacuum level, etc.). The data processing unit 70 might further control operation of the sampling unit 40 (for instance controlling sample injection or synchronization sample injection with operating conditions of the pump 20). The separating device 30 might also be controlled by the data processing unit 70 (for instance selecting a specific flow path or column, setting operation temperature, etc.), and send—in return—information (for instance operating conditions) to the data processing unit 70. Accordingly, the detector 50 might be controlled by the data processing unit 70 (for instance with respect to spectral or wavelength settings, setting time constants, start/stop data acquisition), and send information (for instance about the detected sample compounds) to the data processing unit 70. The data processing unit 70 might also control operation of the fractionating unit 60 (for instance in conjunction with data received from the detector 50) and provide data back.

Reference numeral 90 schematically illustrates a switchable valve which is controllable for selectively enabling or disabling specific fluidic paths within apparatus 10.

In the following, referring to FIG. 2, a sample injector 200 for use in a fluid separation system 10 as described in FIG. 1 for separating components of a fluidic sample in a mobile phase according to an exemplary embodiment of the invention will be explained.

The sample injector 200 comprises a switchable valve 202 (which corresponds to reference numeral 90 in FIG. 1), a sample loop 204 in fluid communication with the valve 202 and configured for receiving the fluidic sample from a vial 230, a metering pump 206 in fluid communication with the sample loop 204 and configured for introducing a metered amount of the fluidic sample on the sample loop 204, and a control unit 208 (such as a microprocessor or a central processing unit, CPU) configured for controlling switching of the valve 202 to transfer the sample loop 204 between a low pressure state and a high pressure state via an intermediate state, as will be described below in further detail. Control unit 208 is further adapted for controlling the metering device 206 to at least partially equilibrate, during the intermediate state, a pressure difference in the sample loop 204 between the low pressure state and the high pressure state. Thus, the metering device 206 (metering pump) is configured to generate a high pressure (in opposite to conventional syringe pumps). This metering device 206 is arranged within the split loop 204. The split loop 204 can be compressed. The precompression may be performed up to a system pressure of the pump 20.

Figure 2:
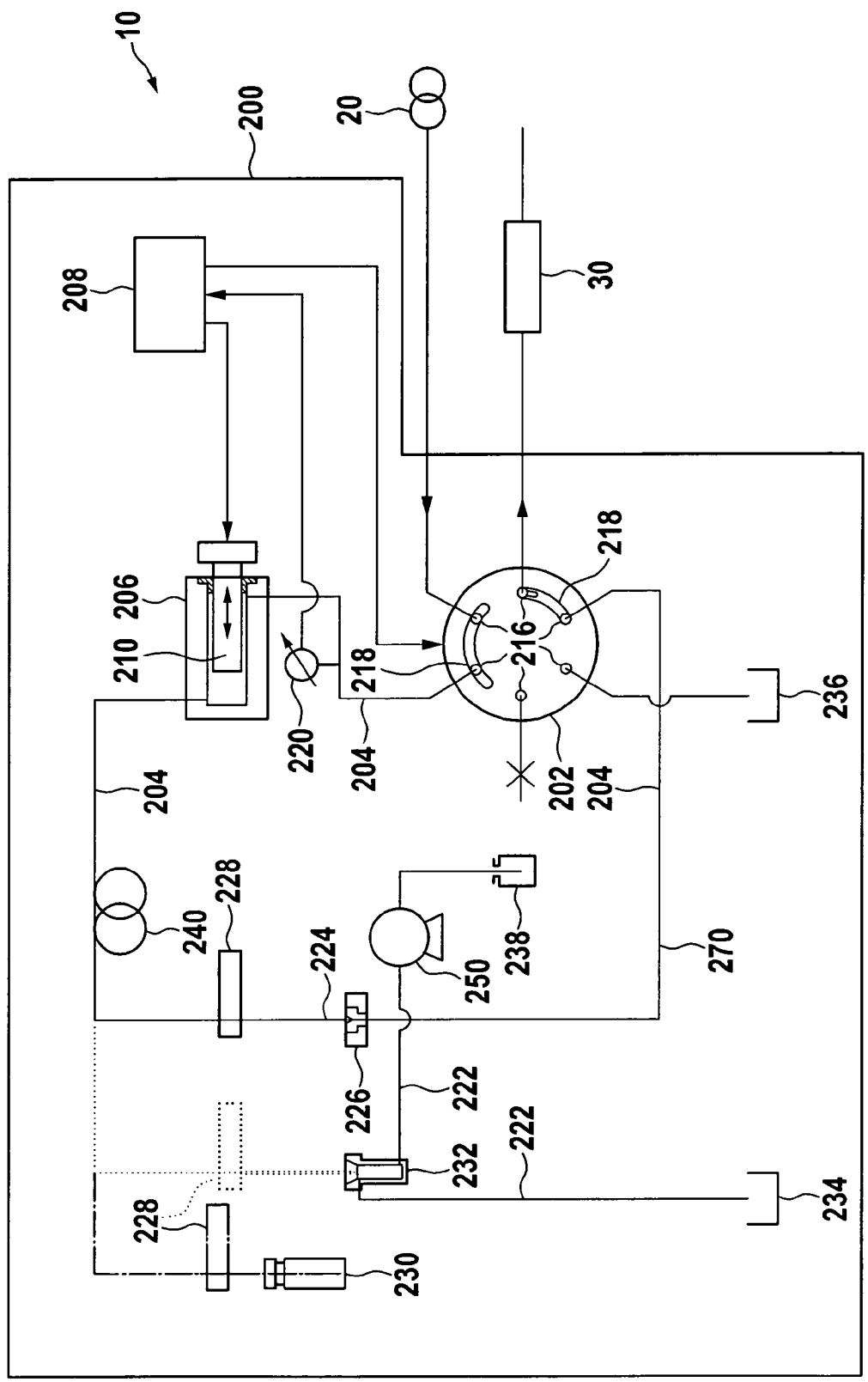
FIG. 2 to FIG. 4 shows an exemplary embodiment of a sample injector according to the present invention in different operation modes.
Figure 3:
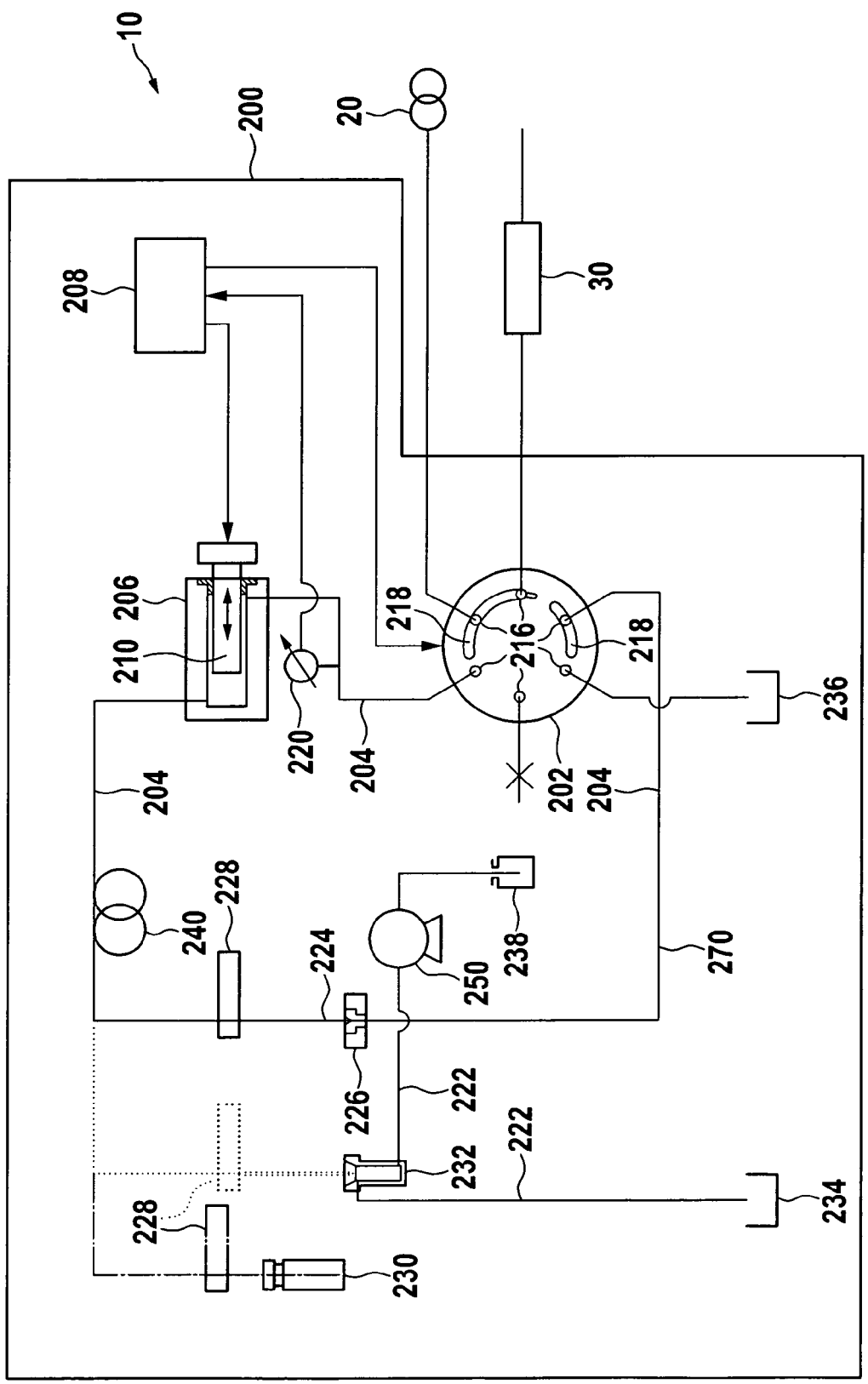
Figure 4:
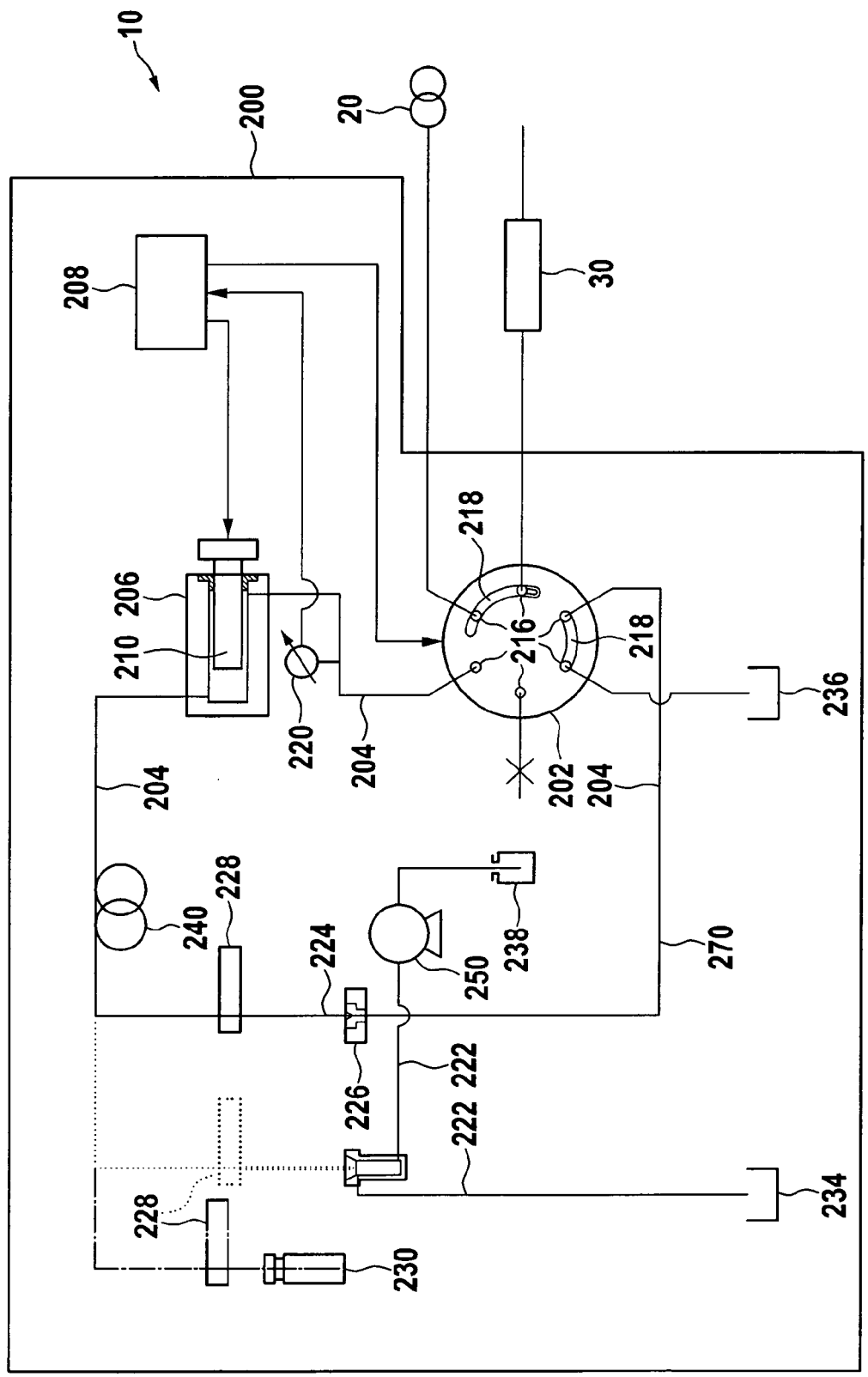

As can be derived from FIG. 2 to FIG. 4, the switchable valve 202 comprises two valve members which are rotatable with respect to one another. By rotating these two valve members along a rotation axis which is perpendicular to the paper plane of FIG. 2, a plurality of ports 216 formed in one of the valve members and a plurality of oblong arcuate grooves 218 formed in the other one of the valve members can be selectively brought in or out of fluid communication with one another. Since the various ports 216 are connected to dedicated ones of fluidic channels of the fluidic system as shown in FIG. 2, automatically switching the valve 202 under control of the control unit 208 may allow to operate the fluidic system 10 in different fluid communication configurations. The valve 202 is configured as a six port high pressure valve in the embodiment of FIG. 2.

Fluid communication between the high pressure pump 20 and the separation column 30 can be accomplished by an according switching state of the valve 202. In such a fluidic path, a high pressure of for instance 100 MPa may be present which may be generated by the high pressure pump 20. In contrast to this, the pressure state in the sample loop 204 may be for instance smaller than 0.1 MPa when introducing a sample into the sample loop 204. When this sample loaded on sample loop 204 is to be loaded on column 30, the pressure in sample loop 204 is also high, for instance 100 MPa.

For the purpose of loading the sample on the sample loop 204, a needle 224 may be driven out of a correspondingly shaped seat 226 using a drive 228 so that the needle 224 can be immersed into vial 230 accommodating a fluidic sample to be loaded onto the sample loop 204. A loop capillary 240 is provided in the sample loop 204 for at least partially accommodating the introduced sample.

In a further operation mode, the needle 224 may be immersed in a flush port 232. Waste containers 234, 236 may be provided for receiving a waste fluid which can be pumped through the fluidic channels shown in FIG. 2. Furthermore, for flushing the fluidic system 200, fluid from a flush solvent vial 238 may be sucked by a peristaltic pump 250 and may be pumped through corresponding channels of the fluidic system shown in FIG. 2.

The metering device 206 is configured as a high pressure metering device, i.e. as a metering device which is capable of providing a pressure of up to 100 MPa in the sample loop 204 by correspondingly moving a reciprocating piston 210 of the high pressure metering device 206.

Before describing further details of the sample injector 200, some basic recognitions of the present inventors will be summarized based on which exemplary embodiments of the invention have been developed.

According to an exemplary embodiment, flow perturbances may be reduced and component lifetime of a HPLC autosampler may be increased by a precompression and/or decompression of its loop volume.

HPLC injection system used for pressures above 60 MPa (for instance 120 MPa) are conventionally faced with various problems. The volume within the split loop (in the embodiment of FIG. 2, the split loop includes particularly high pressure metering device 206, loop capillary 240, needle 224, needle seat 226, seat capillary 270) may be exposed to very high pressures in a main pass position which is illustrated in FIG. 2. Since liquids (mobile phase and sample) under such high pressures are no longer incompressible, this loop volume is being compressed.

Furthermore, switching the injector valve 202 to a bypass position as shown in FIG. 4 conventionally leads to a very fast decompression of the loop volume because it gets connected to atmospheric pressure suddenly. This fast decompression generates a strong acceleration of the liquid which passes with high flow rates through the channels of the injector valve 202. This high flow rate (also called "water jetting") may cause delamination of a coating on the valve stator due to cavitation and erosion on the polymeric valve rotor seal.

On the other hand the pump 20 may deliver flow while the valve 202 switches to a main pass mode shown in FIG. 2. During this time, the valve channel is getting disconnected from the pump 20. The pump 20 is pumping against the closed channel which results in a pressure increase.

At the same time the column 30 gets disconnected from the pump 20 and flow is no longer delivered on top of the column 30. Concurrently the system after the column 30 is open and, via a detector cell, connected to an atmospheric pressure. This may also cause the column pressure to decrease.

The above-mentioned problems of conventional systems which may be overcome by the embodiments shown in FIG. 2 to FIG. 9 have different consequences. Firstly, the jet stream generated during decompression causes damage to the rotor seal and stator of the valve 202. This may result in a reduced valve lifetime. Switching the valve 202 furthermore causes pressure/flow disturbances (perturbances) like pressure peaks. This may lead to precision problems of flow rates, etc. The closed valve 202 causes the column pressure to drop. The reconnected valve 202 on the other hand forwards the flow generated by the pump 20 via the split loop to the column 30. The pressure may be at a reduced level. However, at the beginning of this operation, the column pressure may be still higher than the split loop pressure. In that case there is a possibility for a reverse flow to develop. After this, the pressure starts equilibrating and the pump 20 delivers a positive flow towards the column 30. The pressure peaks and the reverse flow may conventionally reduce the lifetime of a column 30.

Exemplary embodiments of the invention, for instance the systems described in FIG. 2 to FIG. 9 may overcome these conventional problems by taking particularly the measures explained in the following. In order to reduce the observed effects, a modified valve 202 and modified operation procedures are provided. The modified valve 202 has flow channels which are different in length (compare different lengths of the arcuate sections of the grooves 218 in FIG. 2) and the modified operations include stops to provide an intermediate valve state in an inclined position (compare FIG. 3).

By clockwise turning the valve 202 from main pass (or start/inject) position as shown in FIG. 2, the column 30 is connected to the pump 20 via the split loop or sample loop 204. At the inclined position (pre/decompression mode as shown in FIG. 3), column 30 is connected directly to the pump 20. In this inclined position, the split loop (i.e. loop capillary 240 plus metering device 206 plus needle 224 plus seat capillary 270) is now isolated from the pump 20 and the column 30 but is still under high pressure. In order to reduce that high pressure, piston 210 of the metering device 206 can be drawn back a controlled amount for instance until the loop pressure equals atmospheric pressure. For instance, this can be done by using a metering device as disclosed for instance in EP 0,327,658 B1, U.S. Pat. No. 4,939,943 which allows high pressure applications.

With the loop pressure being brought close to atmospheric pressure, the valve 202 can be again turned clockwise to its bypass position which is shown in FIG. 4. This bypass position may also be denoted as a load position. Since there is no pressure gradient between the internal loop pressure and the atmospheric pressure, no water jetting can develop. Therefore, both the delamination of the stator coating and the erosion of the polymer rotor may be eliminated or at least suppressed. The result is an increased lifetime of the valve 202 and of the entire sampling unit 200.

The valve 202 is in the bypass or load position in FIG. 4, and the autosampler is ready to take a sample from vial 230. In a first procedure, the needle 224 may be lifted and moved into the sample vial 230 or a well position (for instance of a multi-well plate). Now, the piston 210 of the metering device 206 may be drawn back to a controlled preset amount (for instance 2 µl). Next, the needle 224 is seated in its seat 226, and the split loop 204 is closed thereby.

The valve 202 is then turned counterclockwise to the inclined position shown in FIG. 3 where the pump 20 is still connected to the column 30. The split loop 204 is closed on both ends. If now the piston 210 of the metering device 206 is moved forward in a controlled manner, its displacement generates a positive pressure and precompresses the trapped volume. This pressure, potentially sensed by a pressure sensor 220, is being increased until it equals the system pressure.

This is the trigger to turn the valve 202 completely to the main pass position which is illustrated in FIG. 2. Because the pressure of the system and the split loop 204 are equal at beginning of this operation, there will be only a very small pressure drop causing only minimum flow disturbances. The pump 20 delivers the mobile phase through the split loop 204 and pushes the sample onto the column 30 where the chromatographical separation of the sample may start.

Hence, FIG. 2 to FIG. 4 show schematically three positions of the injection valve 202 of the autosampler 200 within HPLC system 10 during the injection cycle.

In the main pass position shown in FIG. 2, a start or inject position is shown where the rotor seal flow channels connect pump 20 with the split loop 204 and the seat capillary 270 of the split loop 204 with the separation column 30.

In the inclined position shown in FIG. 3, the split loop volume gets decompressed or precompressed.

In the bypass position shown in FIG. 4, the flow channels of the rotor seal connect the pump 20 directly to the separation column 30 and the split loop 204 to the waste outlet 236.

Next, referring to FIG. 5 to FIG. 9, a sample injector 500 in a liquid chromatography system 10 according to another embodiment of the invention will be explained.

Figure 5:
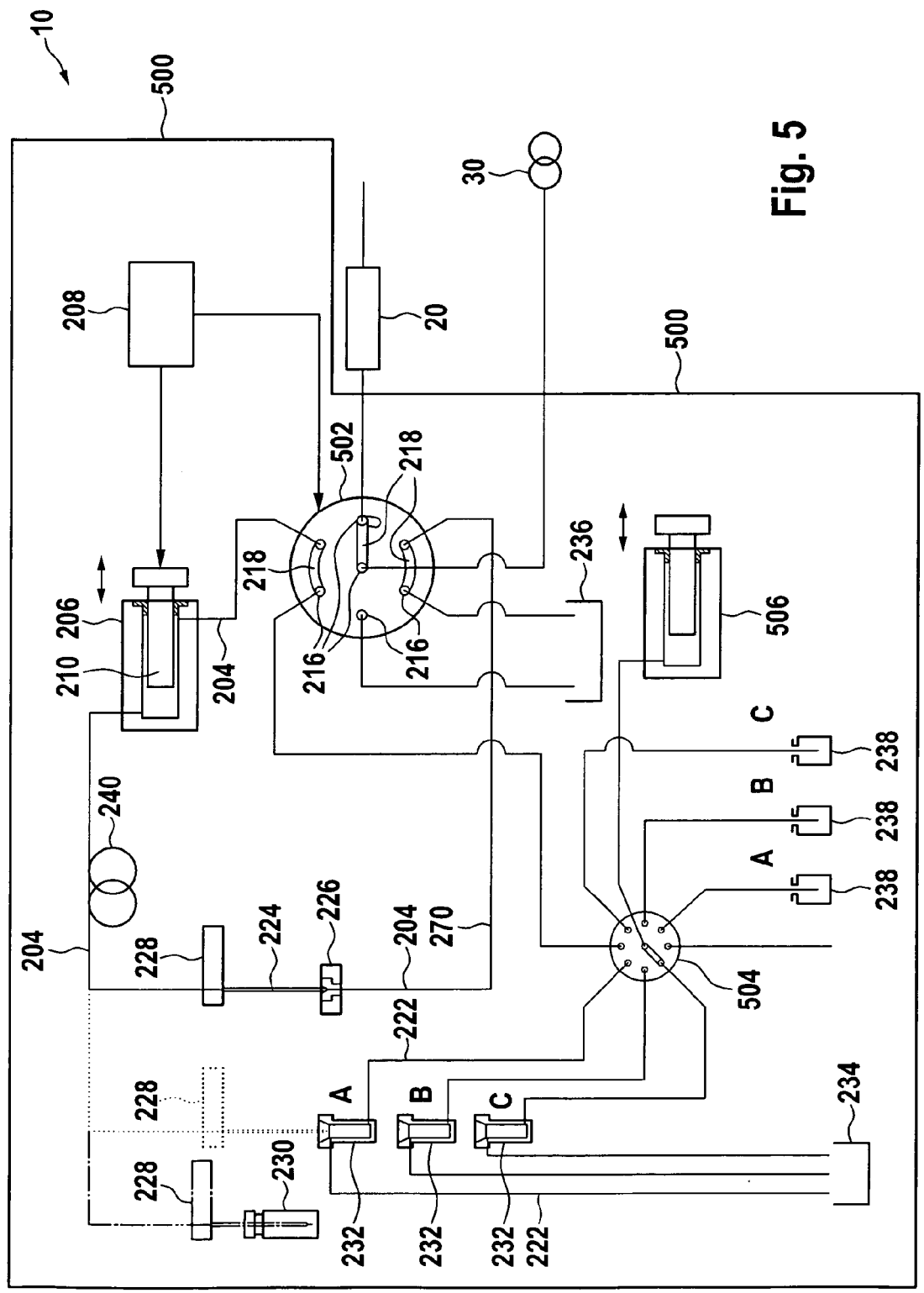
FIG. 5 to FIG. 9 shows another exemplary embodiment of a sample injector according to the present invention in different operation modes.
Figure 6:
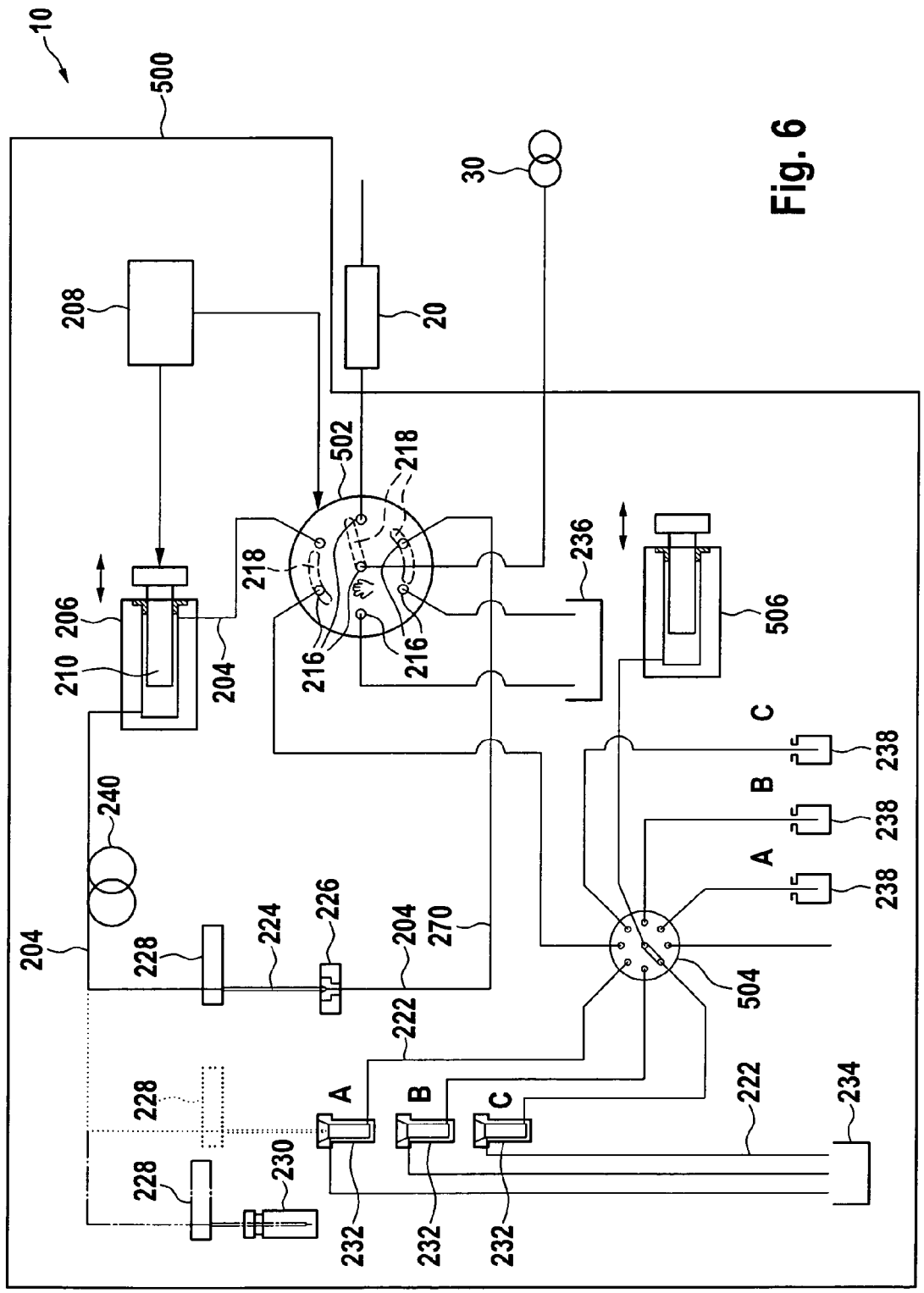
Figure 7:
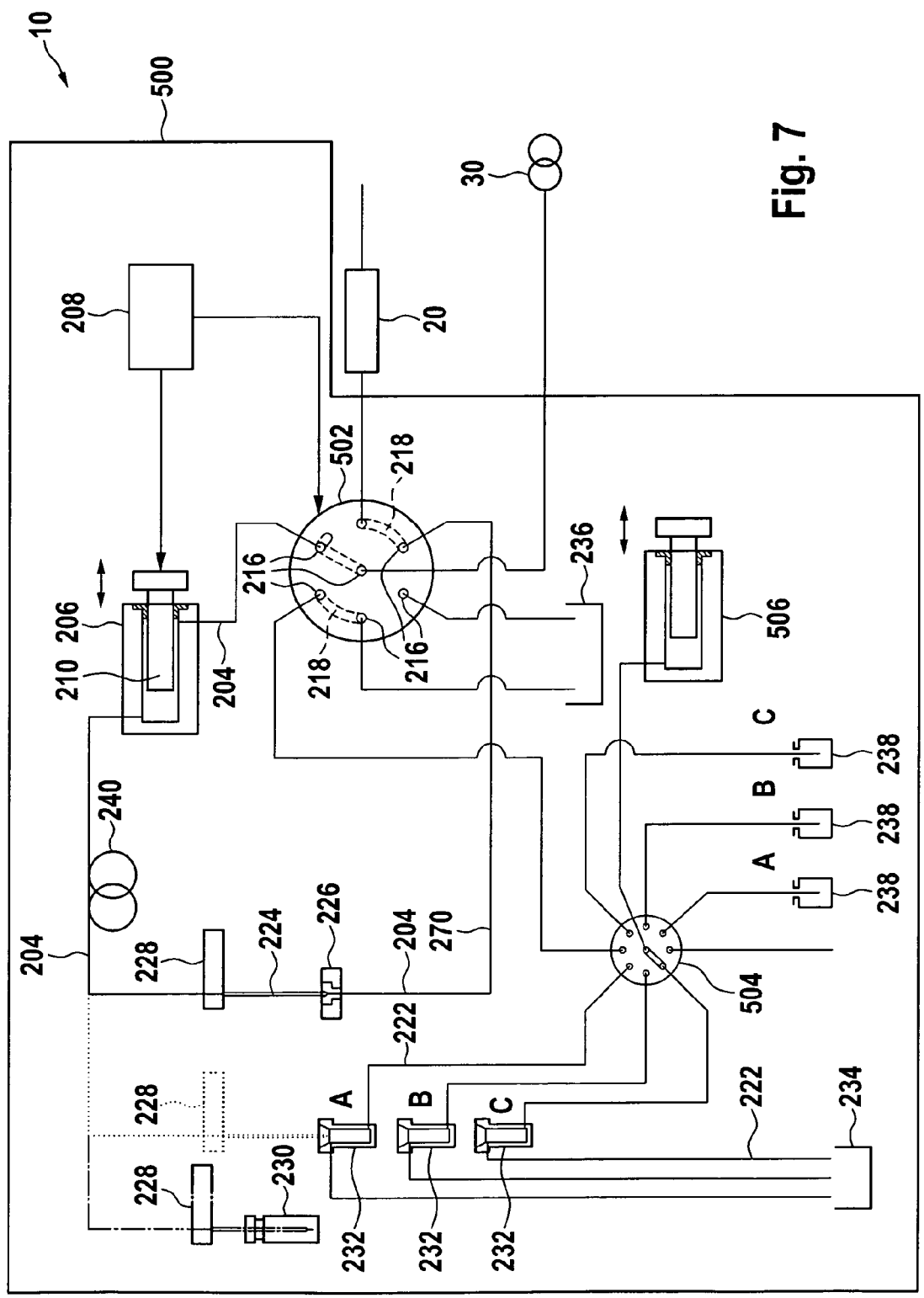

FIG. 5 illustrates a load or bypass position, FIG. 6 illustrates a precompress position and FIG. 7 illustrates an inject position (or main pass position) of the sample injector 500.

A main difference between the sample injector 500 and the sample injector 200 is the arrangement of the valve 502 which in an embodiment of FIG. 5 to FIG. 9 is configured as a multi-position/seven port high pressure valve.

Furthermore, in the embodiment of FIG. 5 to FIG. 9, three different flush solvent vials 238 are provided and three different flush ports 232 are provided. Selection between three flush channels A, B and C can be performed by correspondingly switching a low pressure selection valve 504. Furthermore, a low pressure flush pump 506 is provided for performing the flushing performance.

The multi-position valve 502 is provided for additionally precompressing, pump priming and pressure testing. All drawn sample gets injected. Additional flush pump 506 may be for instance a syringe pump from the company Tecan. Such an additional flush pump 506 may allow flushing of the sample loop 204 using the three flush ports A, B, C (for instance two organic flush ports and one water flush port).

Figure 8:
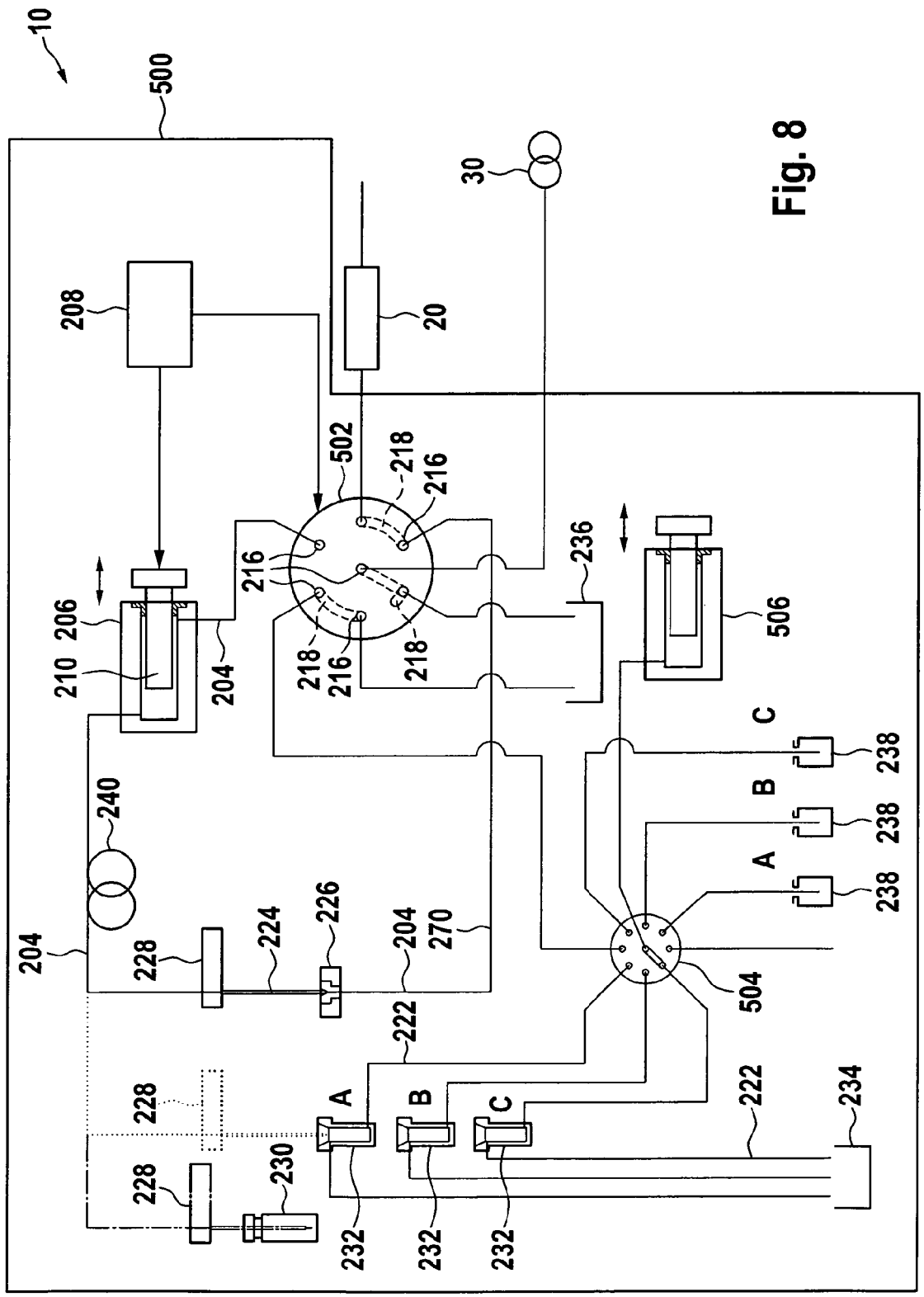
Figure 9:
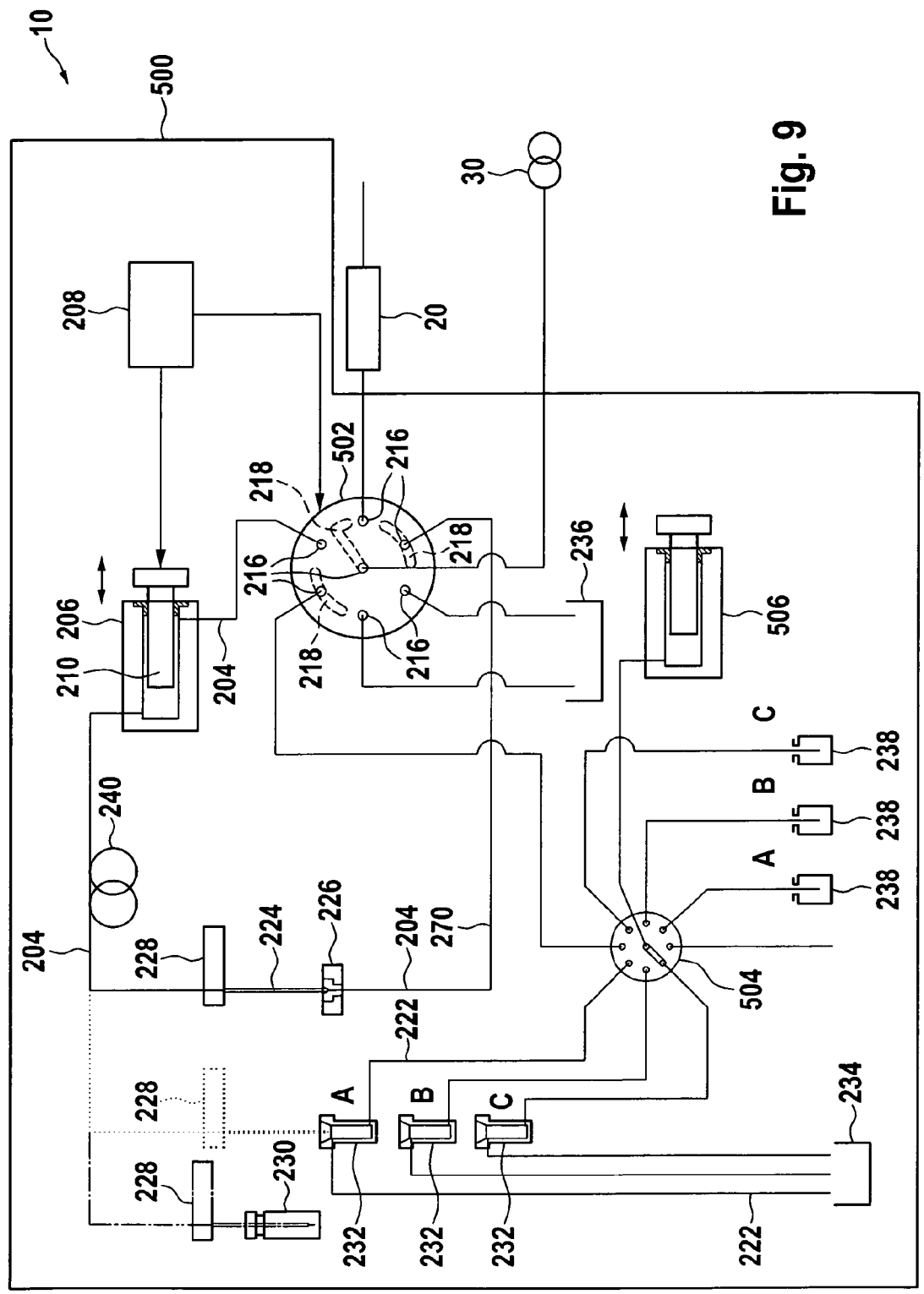

FIG. 8 illustrates the system of FIG. 5 to FIG. 7 in a prime pump position, and FIG. 9 illustrates the system 500 in a pressure test position.

It should be noted that the term "comprising" does not exclude other elements or features and the "a" or "an" does not exclude a plurality. Also elements described in association with different embodiments may be combined. It should also be noted that reference signs in the claims shall not be construed as limiting the scope of the claims.

The invention claimed is:

1. A sample injector for use in a fluid separation system for separating compounds of a fluidic sample in a mobile phase, the sample injector comprising:
a switchable valve;
a sample loop in fluid communication with the valve and configured for receiving the fluidic sample;
a metering device positioned so as to form a part of the sample loop and configured for introducing a metered amount of the fluidic sample into a portion of the sample loop; and
a control unit configured for controlling the valve to switch among a first position, a second position and an intermediate position in order to transfer the sample loop between a low pressure corresponding to the first position of the valve and a high pressure corresponding to the second position of the valve,
the control unit being further configured for controlling the metering device to vary the pressure in the sample loop, while the valve is in the intermediate position, between the low pressure for loading the fluidic sample and the high pressure for driving the mobile phase, wherein the metering device and the sample loop are in fluid communication in each of the first position and the second position of the valve.

2. The sample injector of claim 1, wherein the control unit is configured for controlling the metering device while the valve is in the intermediate position to perform a decompression in the sample loop before transferring the sample loop to the low pressure.

3. The sample injector of claim 2, wherein the control unit is further configured for controlling the metering device for performing the decompression by retracting a metering piston.

4. The sample injector of claim 1, wherein the control unit is configured for controlling the metering device while the valve is in the intermediate position to perform a precompression in the sample loop before transferring the sample loop to the high pressure.

5. The sample injector of claim 4, wherein the control unit is further configured for controlling the metering device for performing the precompression by pushing forward a metering piston.

6. The sample injector of claim 1 wherein the metering device is further configured as a high pressure metering device.

7. The sample injector of claim 1, wherein the metering device is further configured for providing a pressure of about 10 MPa to about 100 MPa as the high pressure.

8. The sample injector of claim 1, wherein the metering device is further configured for providing the same pressure as a mobile phase drive, adapted to drive the mobile phase through a separation column of the fluid separation system.

9. The sample injector of claim 1, wherein the metering device is further configured for increasing the pressure in the sample loop, before the valve is switched from the first position to the second position, to a system pressure of a mobile phase drive, adapted to drive the mobile phase through a separation column of the fluid separation system.

10. The sample injector of claim 1, wherein the valve comprises a first valve member and a second valve member, wherein at least one of the first and second valve members is adapted to be moved with respect to the other, one of the first and second valve members comprises a plurality of ports, and the other comprises at least one groove for fluidly coupling respective ones of the ports in dependency on a relative movement position of the first and second valve members with respect to each other.

11. The sample injector of claim 10, wherein the plurality of ports and the at least one groove are configured such that, when the valve is in the intermediate position and the pressure in the sample loop succeeding the low pressure and preceding the high pressure, a pumping system adapted to drive the mobile phase through a separation column is still in fluid communication with the separation column, and the sample loop is no longer at an atmospheric pressure and not yet in fluid communication with the separation column.

12. The sample injector of claim 10, wherein the plurality of ports and the at least one groove are configured such that, when the valve is in the intermediate position and the pressure in the sample loop succeeding the high pressure and preceding the low pressure of the sample loop, a pumping system adapted to drive the mobile phase through a separation column is still in fluid communication with the separation column, and the sample loop is no longer at a pressure of the pumping system and not yet at an atmospheric pressure.

13. The sample injector of claim 10, wherein the plurality of ports and the at least one groove are configured such that, when the pressure in the sample loop is at the high pressure, the sample loop is in fluid communication with a pumping system adapted to drive the mobile phase through a separation column and is in fluid communication with the separation column.

14. The sample injector of claim 10, wherein the plurality of ports and the at least one groove are configured such that, when the pressure in the sample loop is at the low pressure, the sample loop is not in fluid communication with a pumping system adapted to drive the mobile phase through a separation column and is not in fluid communication with the separation column.

15. The sample injector of claim 10, wherein the plurality of ports and the at least one groove are configured such that a first position of one of the at least one groove is aligned with one of the plurality of ports when the pressure in the sample loop is at the low pressure, a second position of the one of the at least one groove is aligned with the one of the plurality of ports when the pressure in the sample loop is at the high pressure, and a third position of the one of the at least one groove is aligned with the one of the plurality of ports when the pressure in the sample loop is being transferred between the low pressure and the high pressure, the third position defining a stop position of the one of the plurality of ports.

16. The sample injector of claim 1, further comprising a pressure sensor arranged for measuring the pressure in the sample loop and for providing the measured pressure to the control unit as a basis for the controlling of at least one of the metering device and the valve.

17. The sample injector of claim 1, wherein the control unit is further configured for controlling the valve to switch so that a fluidic path in which both the metering device and the sample loop are arranged is selectively brought in or out of fluid communication with a mobile phase drive, adapted to drive the mobile phase through a separation column of the fluid separation system.

18. A fluid separation system for separating compounds of a fluidic sample in a mobile phase, the fluid separation system comprising:
   a mobile phase drive adapted to drive the mobile phase through the fluid separation system;
   a separation unit adapted for separating compounds of the fluidic sample in the mobile phase; and
   the sample injector of claim 1 for introducing the fluidic sample into the mobile phase.

19. A method of operating a sample injector in a fluid separation system for separating compounds of a fluidic sample in a mobile phase, the method comprising:
   introducing, by a metering device, a metered amount of the fluidic sample on a sample loop in fluid communication with a switchable valve and with the metering device;
   controlling the valve to switch among predetermined valve positions to transfer the sample loop between a low pressure and a high pressure; and
   controlling the metering device to increase pressure in the sample loop towards the high pressure state for driving the mobile phase, or to decrease the pressure in the sample loop towards the low pressure state for loading the fluidic sample,
   wherein the metering device and the sample loop are in fluid communication in each of the predetermined positions of the valve.

* * * * *